United States Patent [19]

Davis

[11] Patent Number: 4,753,389
[45] Date of Patent: Jun. 28, 1988

[54] SYSTEM AND METHOD FOR CONTROLLED RELEASE OF VAPORS

[75] Inventor: Norman Davis, Walden, N.Y.

[73] Assignee: American Felt & Filter Company, Newburgh, N.Y.

[21] Appl. No.: 22,117

[22] Filed: Mar. 5, 1987

[51] Int. Cl.$^4$ .............................................. A61L 9/12
[52] U.S. Cl. ............................................ 239/6; 239/56
[58] Field of Search ...................................... 239/34–60, 239/6

[56] References Cited

U.S. PATENT DOCUMENTS

| | | | |
|---|---|---|---|
| 1,732,028 | 10/1929 | Reiner | 239/59 |
| 3,419,217 | 12/1968 | White et al. | 239/58 |
| 4,159,631 | 7/1979 | Lee | 239/36 |
| 4,277,024 | 7/1981 | Spector | 239/36 |
| 4,356,969 | 11/1982 | Obermayer et al. | 239/56 |

Primary Examiner—Andres Kashnikow
Assistant Examiner—Michael J. Forman
Attorney, Agent, or Firm—Martin Smolowitz

[57] ABSTRACT

An improved system and method for providing a controlled release of vapors from a vaporizable material such as a fragrance material provided in a container for air freshening. The system includes a sealable container containing a porous reservoir medium, which contains a liquid fragrance material in communication with a plenum cavity for accumulation of vapors therein without reaching a pressure equilibrium with the liquid source. A permeable barrier is provided between the plenum and the atmosphere for metered release of vapors through an aperture provided in an impermeable barrier to the atmosphere. The reservoir medium contains capillaries and the surface area of the reservoir medium adjacent the plenum is made large compared to that of the apertures in the impermeable barrier. Thus, the conversion of a liquid phase fragrance material in the reservoir absorbent material to vapor phase for dispersal to the surrounding air is controlled so that the service life of the device is substantially extended. A method for making and using the fragrance dispersing system is also disclosed.

17 Claims, 4 Drawing Sheets

SYSTEM AND METHOD FOR CONTROLLED RELEASE OF VAPORS

BACKGROUND OF INVENTION

This invention relates generally to the controlled release of vapors from a liquid source. It relates more particularly to the controlled release and dispersal of aromatic vapors for air fragrance and/or freshening by a system and method for controlled metering and release of such vapors from a liquid source to the surrounding atmosphere.

Room air fresheners typically function by absorbing or masking unpleasant odors. Manufacturers of such air freshener devices or products must predetermine the relationship needed between absorptive or masking capacity of a given fragrance material formulation, the desired useful life-span for the material, and mechanisms capable of delivering the desired fragrance or freshening effect to a surrounding space. In the class of air freshener devices whereby an aromatic formulation is allowed to vaporize into the air around it, thereby masking whatever other odors may be present, the useful life of the air freshening device is determined by the total volume of volatile material available, the vapor pressure of the volatile material, and the exposed surface area from which the volatile material can escape.

The prior art for the manufacture of such air freshener devices does not permit the use of aromatic formulations which have high vapor pressures, because these fluids evaporate relatively rapidly, thus producing an undesirably short usable life-span for the product. The use of stabilizers, fixatives and the like in such aromatic formulations can result in these additives accumulating at the surface intended for evaporation, thereby effectively blocking evaporation of the aromatic material to any useful degree and at the same time thwarting the intended use of any device using fluids containing such formulation. For this reason, fragrances containing such formulations having high vapor pressures are not typically used, and in general such formulations and those with high vapor pressures are avoided by the air freshener industry as unusable. Thus, the range of useful fragrance materials is thereby undesirably limited.

Also, various other prior art devices have been provided which are intended to control the release of vapors such as from deodorants, disinfectants or fragrances. For example, U.S. Pat. No. 2,412,326 to Dupuy discloses a vaporizing device in which the vaporization rate of material from a container is controlled by a cover having variable area openings. U.S. Pat. No. 2,111,025 to Galler discloses an unitary vapor generating device containing dual compartments which are each sealable by removable adhesive seals. Also, U.S. Pat. No. 2,572,329 to Foster discloses a room deodorizer including a container having a porous stopper element attached to a wick for controlling the rate of liquid evaporation from the container, the deodorizer being resealable by a screw top. U.S. Pat. No. 4,157,787 to Schwartz discloses an air freshener dispenser having a first layer of porous material covered by a second layer of non-porous material. Although these devices have been found useful, a need still exists for an improved vapor release system for the controlled release of vapors, particularly from more concentrated fragrance generating material sources having high vapor pressures.

SUMMARY OF INVENTION

The present invention has as its primary object to provide a system and method for improved delivery or release of vapors from a predetermined volume of volatile fluid or mixture for an extended predetermined period of time.

A particular object of the invention is to provide an improved vapor release control system and method for delivering socalled air-freshening aromatic vapors from a reservoir container to the surrounding ambient air at a controlled slow rate.

In attaining these and other objectives, the invention provides a sealable container containing a reservoir porous material or medium having a size and shape appropriate to the physical properties of a vaporizable fluid, such properties including but not limited to specific gravity, viscosity, surface tension, and vapor pressure. A hermetically sealable cavity of plenum is provided adjacent an exposed side of the reservoir material, and is suitable for accumulation of vapors of the aforementioned vaporizable fluid, such that these vapors approach but usually do not reach a pressure equilibrium with the liquid-phase fluid contained in the reservoir medium. The invention also provides for the controlled and metered release of the vapors from the sealable plenum through a partial barrier provided by a permeable barrier medium located adjacent the plenum, the properties of the permeable medium being determined by the volume of vaporizable fluid contained in the reservoir medium and the desired period of time during which the fluid is to continue to evaporate from the reservoir. The permeable barrier material is preferably covered by an impermeable barrier material containing at least one aperture, which aperture is covered by a removable hermetic seal prior to use.

In preferred practice, the invention combines a reservoir porous material in which the exposed surface area is a relatively large multiple of the effective exposed area of the permeable barrier medium intended for the metered release of vapors arising from the reservoir. Also, the reservoir material exposed surface area should be at least 50 times the total area of the apertures in the impermeable medium, and preferably 75–300 times the aperture total area. The result is that the conversion or evaporation rate of liquid phase vaporizable material contained in the reservoir material to vapor phase is effectively controlled, and this evaporation control in turn controls the rate of vapor flow successively through the plenum space, permeable barrier medium, and aperture(s) in the impermeable barrier material for dispersion to the atmosphere surrounding the system or device. Surface area multiples for the exposed reservoir material compared to the aperture total area between 75:1 and 200:1 have been found to be effective in extending and controlling the dispersion rate of high vapor pressure fluids from less than 90 hours to a useful life over 1000 hours.

The invention also includes a method for releasing vapors from a vaporizable liquid material within a container to the ambient air at a controlled slow rate. The method steps used include providing a vaporizable liquid material having a desired threshold of perceptibility in terms of its air concentration in a desired volume of an absorbent reservoir material, the reservoir material having a void percentage and a reservoir volume sufficient to retain the desired fluid volume; selecting a predetermined time period required for the vaporizable liquid to be evaporated and dispersed; providing a permeable barrier material having a gas permeability of 1-100 cfm/sq. ft./0.5" water differential pressure near an external surface of the reservoir material so as to provide a plenum space therebetween; providing an impermeable barrier having at least one aperture of controlled total area adjacent the permeable barrier material, and enclosing the selected materials in an appropriately dimensioned hermetically sealable container having a removable seal provided covering the aperture. Whenever it is desired to commence a controlled release the vapors from the vaporizable material to the surrounding atmosphere, the seal is removed thereby allowing the vaporizable liquid to evaporate and to be released to the surrounding atmosphere at a desired controlled rate for a predetermined period of time.

The present invention is useful for the controlled dispersing of vaporizable liquids and solids having vapor pressures exceeding 760 mm Hg at normal room temperatures of 50°–100° F. Vaporizable liquid materials for which the invention is useful include fragrances and air freshener formulations utilizing solvent solutions of essential oils including fixing and stabilizing agents, and germicidal disinfectant materials.

The foregoing and other objects and features of the invention will be apparent from the ensuing detailed description of preferred embodiments thereof and from the following drawings, wherein like reference numbers identify like parts.

DESCRIPTION OF PRIOR ART AND PREFERRED EMBODIMENTS

Figure 1:
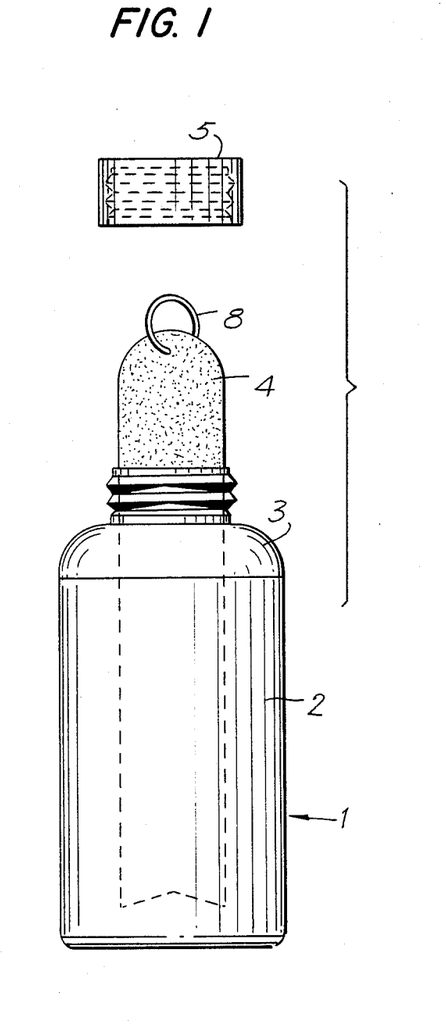
FIGS. 1–4 are schematic sketches showing prior art fragrance dispersing devices utilizing various constructions and methods of use.

Referring first to FIG. 1, there is shown a wick-type device in which a container 1 containing a vaporizable liquid 2 is absorbed by a wick 4 which also acts as a reservoir 3 for the fluid 2. Upon lifting the wick 4 from the container 1 by means of handle ring 8, the fluid 2 is exposed to the surrounding air. When the device is not in use, the wick 4 is pushed back into the container 1 and secured by a threaded cap 5 which is fluid-tightly sealed to the container 1. The vaporizable liquid remains in liquid form in the container.

Figure 2:
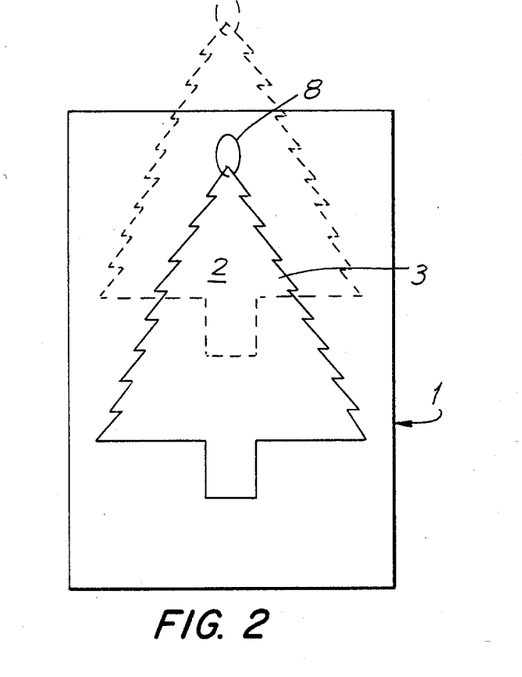

Referring to FIG. 2, a reservoir type device is shown in which a fragrance material 2 is impregnated into an absorbent pad in reservoir 3, which can have various shapes and is sealed in a pouch 1. Upon use, the consumer opens the pouch 1 and draws out a small portion of the absorbent reservoir material 3 by means of a hanger thread 8. As the exposed fragrance material 2 is dissipated, more material can be exposed by withdrawing more of the reservoir 3 until the pouch 1 is empty and can be discarded.

Figure 3:
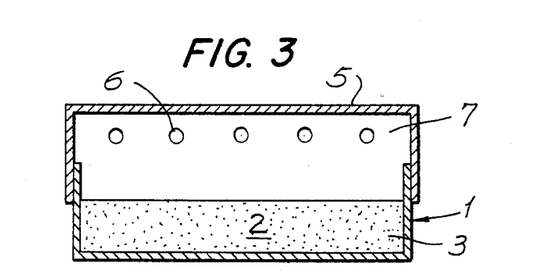

Referring to FIG. 3, a chamber type device is shown in which an aromatic fragrance material 2 is blended with a wax-based material forming a cake reservoir 3 which is enclosed in a container 1. In use, the consumer turns the apertured cover 5 so as to allow air to enter apertures 6 and move across the surface of the cake 3 through an air space 7 therein.

Figure 4:
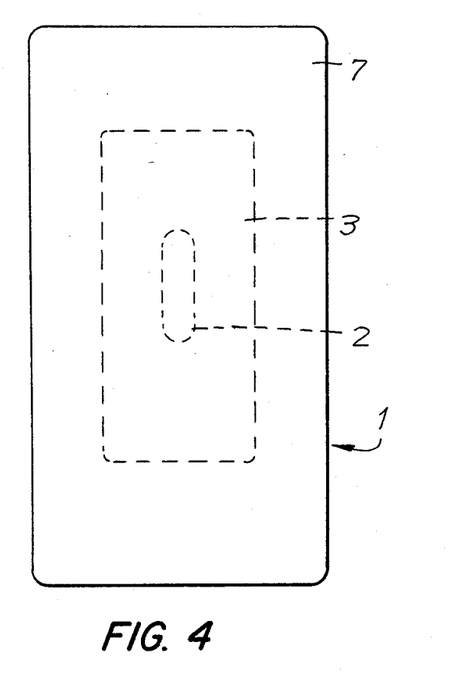

Referring also to FIG. 4, an aromatic material 2 is enclosed in an ampule which is wrapped in an absorbent pad 3 and enclosed in a permeable pouch 1. The permeable pouch permits escape of molecules of the fragrance material 2 due to a property called molecular sieve permeation through the pouch permeable walls.

Consumer experience with the types of fragrance-emitting devices shown in FIGS. 1–4 and described above include general dissatisfaction and problems with fluid leakage, staining, and early termination of service for each device. Specifically, the fluid contained in the FIG. 1 wick-type device can be spilled and will stain, causing damage to fabrics or furniture. With the FIG. 2 reservoir-type device, the pouch cover can tear and fall off, allowing premature and undesired excessive escape of the fragrance material and early termination of service. In FIG. 3 closable chamber type units, the performance level is initially high, but decays rapidly during use and control of vapor release is inadequate. In FIG. 4 pouch type units, the variety of fragrance materials which will penetrate the molecular sieve barrier wall is extremely limited, thus seriously limiting its utility.

Figure 5:
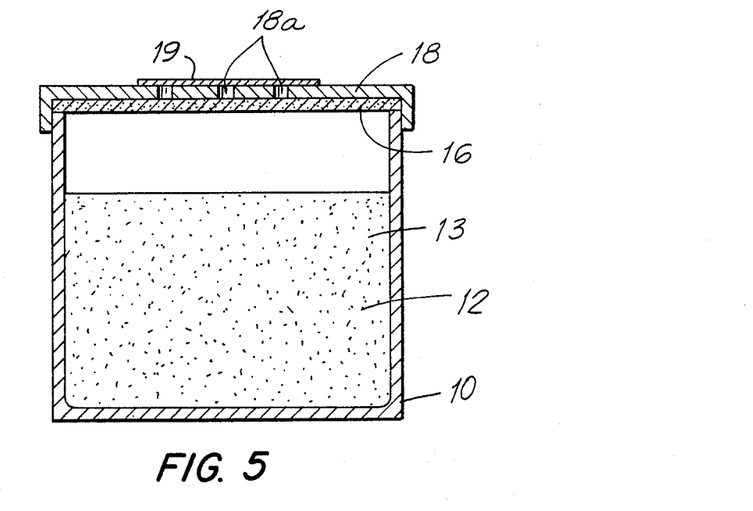
FIG. 5 is a schematic sectional drawing of a fluid dispersing system and method according to the present invention.

Referring now to the FIG. 5 configuration showing the present invention for a vapor-releasing device, a hermetically sealable chamber or container 10 has a vaporizable fragrance material 12 dispersed in an absorbent reservoir material 13 provided inside the container. Located above the reservoir 13 there is a plenum chamber or space 14, which is covered by a porous medium barrier 16. The outer face of permeable barrier 16 is further covered by an impermeable barrier 18 in which there is provided at least one and usually a plurality of apertures 18a. The apertures 18a are temporarily further sealed by a removable hermetic seal 19 used for purposes of storage and shipping of the device before its use.

For use of the fragrance releasing device, the consumer first removes the hermetic seal 19 which exposes the apertures 18a to the surrounding atmospheric environment. The fragrance releasing aromatic fluid material 12 is now able to evaporate from the reservoir 13 into the plenum 14, forcing both trapped air and vapor out through the porous barrier 16 and thence through apertures 18a into the surrounding atmosphere. This device is an improvement over prior art vaporizer devices such as disclosed by U.S. Pat. No. 2,412,326 to Dupuy, in that changes in atmospheric air pressure and temperature are substantially isolated from the interior of the fragrance-emitting device, thereby permitting the device to function more independently of the surrounding environment than for the prior art devices.

In significant contrast to dissatisfied consumer experience with the prior art types of fragrance dispersing devices described by FIGS. 1 to 4 above, the present invention as shown in FIG. 5 and described above eliminates leakage and staining by the fragrance material, which cannot spill and cannot be over-exposed. Furthermore, the device is not limited to use with only a small class of fragrance releasing materials, but has wide application to many vaporizable liquid and solid materials.

In the present invention all elements used are subject to technical control, so that the consumer or user can be assured of a repeatable, reliable performance for the fragrance releasing device. Such technical control for elements of the device are further described hereinbelow.

First, the container 10 can be modified to have any desired size, shape or material composition, to accommodate the characteristics of volume and composition of both the vaporizable fragrance material 12 and the reservoir absorbent material 13. The fragrance material 12 used can be blended with other materials or modified to provide any desired properties of specific gravity, viscosity, surface tension and vapor pressure, determined to be suitable for a particular fragrance or disinfectant releasing application. Useful fragrance-releasing materials include any of many known essential oils and synthetic aromatic materials, which are usually dissolved in suitable organic solvents such as alcohols to produce a desired fragrance formulation, with essential oils usually being preferred because aesthetic desirability renders them so empirically. Also, various fixing agents and/or stabilizers can be utilized with the essential oils and aromatic materials in particular formulations. For example, an essential oil useful for the invention is menthol and a useful aromatic material is ethyl acetate both dissolved in an alcohol solvent.

Second, the reservoir absorbent material 13 can be selected from a wide range of porous materials including felts, foams, paper products and the like, and which have a void volume needed to contain and support the predetermined volume of liquid fragrance material and a level of capillarity adequate to retain a particular fluid within the reservoir without leakage. This level of capillarity for the reservoir material also is fundamental and required to continuously redistribute the fluid fragrance material, as the fluid vaporizes at the exposed surface of the reservoir material into plenum chamber 14. The porosity or voids fraction of the reservoir material 13 should be as high as possible consistent with the capillary needs of a particular absorbed fluid and reservoir material shape. The reservoir voids fraction should normally be at least about 75%, and preferably 85-95% voids.

Figure 6A:
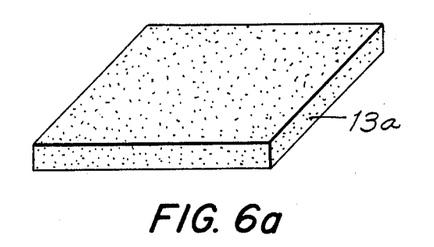
FIG. 6 is a perspective sketch showing some specific structure shapes useful for controlling the surface area of the reservoir material used in the invention.
Figure 6B:
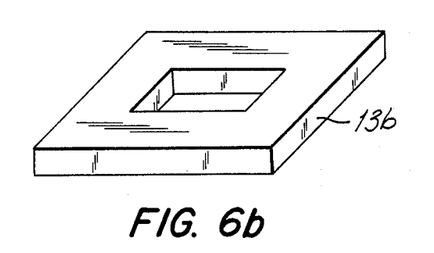
Figure 6C:
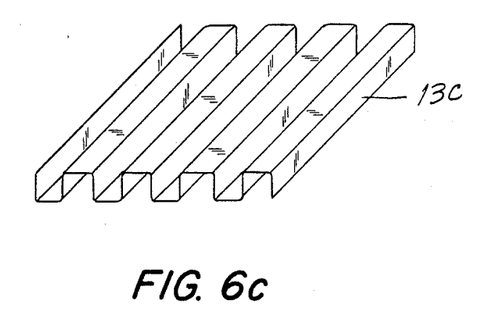

The exposed surface area of the reservoir material 13 can be modified by various means including use of a basic fibrous or porous pad as shown in FIG. 6a, a perforated surface such as shown in FIG. 6b, or a corrugated or pleated structure, such as illustrated in FIG. 6c. Control of the relationship between total volume occupied by the outside dimensions of the reservoir material 13 and the exposed surface area of the reservoir material adjacent the plenum 14 is a principal factor for controlling the volume and evaporation rate of a fragrance material as used in this invention. In most cases, cutting or shaping the reservoir material to increase surface exposure reduces the volumetric absorption capacity, hence there is a point at which the gross spatial dimensions of the reservoir might need to be increased to restore the necessary capacity.

Third, the plenum chamber 14 can be controlled in size, shape, total volume, and spatial disposition with respect to the reservoir 13, the only critical parameter being that the plenum 14 be located between the reservoir 13 and the porous barrier 16.

Fourth, the porous barrier material 16 can be composed of any material which is permeable to the passage of vapor. Filter media typically represent such porous materials, and are permeable within the limits of 0.1 to 600 cfm/sq. ft./0.5" H2O, and preferably have permeability of 1-100 cfm/sq. ft./0.5" H2O, more preferably being 2-25 cfm/sq. ft./0.5" H2O differential pressure.

Fifth, the impermeable barrier 18 can be any solid material which is cuttable, glueable or otherwise adherable to the permeable membrane 16. Plastic films are impermeable within the scope of the invention, with molecular sieves being specifically excluded as having excessive permeability and thus being unsuitable for the impermeable barrier material 18.

Sixth, the apertures 18a provided in the impermeable barrier film 18 provide a means whereby the total exposed surface area of the permeable barrier 16 is controlled between 0% (totally impermeable) and 100% (natural permeability of the permeable barrier 16).

Furthermore, the combinations of each of the above six controllable elements of the vapor release device according to the present invention are also controllable in various ways or combinations, such that for example, a large capacity reservoir material 13 could be combined with a small volume plenum 14 and highly permeable barrier 16 to accommodate fragrance materials having low vapor pressure or a high threshold of perceptibility. Conversely, a relatively small capacity reservoir 13 could be combined with a large volume plenum 14 and highly permeable barrier 16 for a "bomb" type air freshener, where it is desirable for a large volume of fragrance material vapor to be dispersed rapidly during a short time period. Thus, there is usually no most desirable preferred combination of the elements since a principal feature of the invention is its adaptability to the properties of a given fragrance material or family or class of fragrances.

More specifically regarding the method steps of the invention, first a desired vaporizable liquid fragrance material formulation such as having a lemon or mint odor is selected and its characteristics of percent volatile fraction, threshold of perceptibility, (the amount evaporated into a standardized air volume that can be smelled by an experienced observer), and its free evaporation rate are determined. Next, for a selected useful time period or operational life for a fragrance release device such as 1000 hours, the required quantity of the fragrance material is determined. Next, an absorbent reservoir material is selected, such as a polyester felt material, and its percentage void volume determined, after which the required volume of reservoir material needed to absorb the required quantity of fragrance material can be determined by calculation, and also desired outer dimensions for the reservoir material are determined. Then, based on the fragrance material free evaporation rate and its threshold of perceptibility, and the permeability of a selected porous barrier material, the required total aperture area is calculated for a fragrance release device having the desired useful life. Then, after the parameters of the selected elements of the device have been determined, the elements are assembled essentially as shown in FIG. 5 and as described hereinabove.

This invention will be further described with reference to the following Examples of functioning vapor release devices, which should not be construed as limiting the scope of the invention.

EXAMPLE 1

One example of a device for controlled vapor release from a vaporizable liquid and constructed similarly to that shown in FIG. 5 in the form of a cannister consists of the following elements:

(a) a 4-ounce size screw top container jar with a cover having an 1-inch diameter hole in the middle of the cover;

(b) a reservoir material consisting of a needled or punched felt material composed of 3 denier polyester fibers, weighing 105 ounces per square yard and having thickness of 0.625 inch, and formed in the shape of two washers each having an outside diameter of 2 inches and an inside diameter of 1 inch, the two washers combined being saturated with 30 grams of a liquid fragrance material. This reservoir material has a void fraction of 85%. The total volume of fragrance material is 41 cc, leaving 11 cc of space to provide a safety margin for variation in parts and liquid charge;

(c) a plenum of 0.5 inch wide vacant space within the jar described in (a) above between the cover and the reservoir material;

(d) a permeable medium consisting of a polyester fiber filter felt composed of 100% 3 denier polyester fiber, weighing 11 ounces per square yard, being 0.07 inches thick and having an air permeability of 110 cfm/sq. ft./0.5" $H_2O$ differential pressure; and (e) an impermeable barrier, consisting of an adherable polyester film, (specifically duPont Mylar) of 3 mil thickness, in which there is a single perforation of either 2.6 square centimeters or 7.6 square centimeters area. The impermeable barrier is thermally adhered to the permeable membrane described in (d) above, the combination being then cut to form a self-gasketing seal under the jar perforated cover described in (a) above.

This unit was assembled as an example of a cannister type vapor release device similar to FIG. 5. This construction of a vapor release device would be suitable for location in closets, on shelves or under furniture, where it is out of the way.

Evaporation rate data were obtained on 4 fragrance materials which were evaporated independently of the device, and one of these fragrances was evaporated within two samples of the device as constructed above. The four fragrance materials identified as numbers 12, 13, 14 and 15 were exposed to the atmosphere in an open cup under ambient conditions and were found to evaporate at various rates, depending on their composition and existing conditions of temperature and atmospheric pressure, as shown below.

| Fragrance No. | Fragrance Material Evaporation Rate Grams/sq.cm./hr | |
|---|---|---|
| | Slowest | Fastest |
| 12 | .0004 | .0014 |
| 13 | .0008 | .0032 |
| 14 | .0002 | .0015 |
| 15 | .0004 | .0011 |

Fragrance #15 was placed in two separate samples of the device described above. Each sample device contained 30 grams of fragrance #15, shown above to vaporize in open air at a rate between 0.0004 and 0.0011 grams/sq.cm./hour. The two sample devices each had constant volume absorbent reservoir pads to contain the fragrance material, constant volume plena, and different aperture areas being 2.6 and 7.6 sq.cm. The test units were each exposed over 500 hours, with the following results:

| Test Device No. | 1 | | 2 | |
|---|---|---|---|---|
| Fragrance Charge, grams | 30.0 | | 30.0 | |
| Reservoir exposed area, sq.cm. | 392 | | 392 | |
| Aperture area, sq.cm. | 2.6 | | 7.6 | |
| Area ratio reservoir/aperture | 151 to 1 | | 52 to 1 | |
| Elapsed time, hrs. | Loss, grams | Loss Rate Gms/sq.cm./hr | Loss grams | Loss Rate Gms/sq.cm./hr |
| 165 | 0.7 | .0016 | 1.9 | .0015 |
| 237 | 1.0 | .0016 | 2.4 | .0013 |
| 380 | 1.7 | .0017 | 3.4 | .0012 |
| 500 | 2.0 | .0015 | 4.3 | .0011 |
| Extrapolated useful life of device, hours | | 7500 | | 3500 |

These data demonstrate the effect of aperture size on performance of the device, everything else being equal. It is noted that the test device having the larger aperture exhibited the greater total loss of fragrance material over time, with the fragrance evaporation or loss rates being similar for each device. Theoretically, the fragrance loss rates should be the same for both devices, the differences being attributable at least in part to measurement error in aperture size and weight measurement error (0.1 gram accuracy). It is also noted that for each unit the fragrance loss rate slowed down with elapsed time due to changes in the volatile fraction of the residual fragrance.

EXAMPLE 2

Another exmple of a vapor controlled release device constructed within the scope of this invention utilizes a flexible pouch-like configuration, and consists of the following elements:

(a) a reservoir pad of 3 denier polyester felt having density of 15 ounces per square yard, 0.32 in. thick and cut into a rectangle shape 2.875×2.375 inch size;

(b) a plastic screen separator of large mesh size, having openings approximately 0.5 in. square and cut to size 2.875×2.375 in. to provide a plenum space adjacent the felt pad;

(c) two permeable media each having permeabilities of 6.5 and 25 cfm/sq.ft./0.5 in. $H_2O$ differential pressure respectively;

(d) a bondable impermeable 3 mil polyester film having a single aperture of 0.227 $cm^2$ area, this film being adhered to the permeable media described above in (c), and then cut to the size 2.875×2.375 in.

These elements were assembled as a stack in the order listed above and then wrapped in aluminum foil with the apertures of (d) above exposed, the foil being sealed in place with plastic tape to form a hermetically sealed pouch, except for the aperture.

Each pouch reservoir pad was charged with a single fragrance formulation #13 listed in Example 1. This type construction would be suitable for automatic installation in fan-dispersed institutional air fresheners.

Tests on two pouches were conducted at 100° F. temperature to accelerate the rates of evaporation of the fragrance material. Data on these pouches, consisting of nearly identical conditions except for the different permeable media mentioned in (c) above, are as follows:

| Test Device No. | 3 | 4 |
|---|---|---|

-continued

| | | |
|---|---|---|
| Fragrance charge, grams | 20.0 | 20.0 |
| Aperture area, sq. cm. | 0.227 | 0.227 |
| Permeable barrier material | polypropylene felt 10 oz. sq. yd. 1 in. micron filter | tightly woven nylon mesh |
| Permeable barrier porosity, cfm/ft$^2$/0.5 in. H$_2$O | 6.5 | 25 |
| Reservoir surface area, sq. cm. | 44.5 | 44.5 |
| Reservoir exposed area/aperture area ratio | 200:1 | 200:1 |

| Device Exposure, hours | Cumulative Exposure, hours | Fragrance Loss, grams | Fragrance Loss Rate, gms/sq. cm./hr | Frag. Loss, gms. | Frag. Loss Rate gms/sq. cm./hr. |
|---|---|---|---|---|---|
| 20 | 20 | 0.0 | 0.0 | 0.3 | .0661 |
| 96 | 116 | 0.7 | .0267 | 1.6 | .0608 |
| 48 | 164 | 1.1 | .0295 | 2.2 | .0591 |
| 144 | 308 | 1.7 | .0100 | 3.0 | .0429 |

These data demonstrate the effect of changes in permeability of the permeable barrier for a constant size aperture, with the permeable barrier material having the greater porosity providing the greater evaporation rate for the fragrance material.

It will be understood that modifications and variations can be made within the spirit and scope of the invention, which is defined by the following claims.

I claim:

1. A vapor release system for dispersing vapors from a vaporizable material in a controlled manner, comprising:
   (a) a hermetically sealable container;
   (b) a porous reservoir material provided within said container and containing a vaporizable material; said reservoir material having capillarity sufficient to continuously move the vaporizable material to an exposed surface of said reservoir material at a slow rate which prevents flooding or leaking of liquid from the reservoir material;
   (c) a plenum space provided within said container adjacent the exposed surface of the reservoir material;
   (d) a permeable barrier material located adjacent said plenum, so that said plenum space is located between the reservoir material and the permeable barrier, said permeable barrier material having a porosity of 0.01–600 cfm/ft$^2$/0.5 in. water differential pressure;
   (e) an impermeable barrier containing at least one aperture located adjacent said permeable barrier, whereby said permeable barrier and said aperture in the impermeable barrier provide a combination permitting vapors to escape from the plenum at a predetermined low rate so that the vaporizable material absorbed in said reservoir material is controllably evaporated from the reservoir into said plenum and then released at a controlled rate through the permeable barrier and then through the aperture to the surrounding atmosphere.

2. The vapor release system defined in claim 1, wherein said permeable barrier material has a permeability sufficiently low to permit development of a vapor pressure in said plenum space.

3. The vapor release system defined in claim 1, wherein said porous reservoir material exposed surface area is at least about 50 times the area of said aperture in said impermeable barrier.

4. The vapor release system defined in claim 3, wherein said reservoir material exposed surface area is 100–300 times the area of said aperture in said impermeable barrier.

5. The vapor release system define in claim 1, wherein said reservoir material has a void fraction volume of at least 75% and a volumetric capacity commensurate with the vaporizable material volume required, such that when the vapor is released at a predetermined rate it will provide continuous release of vapor for a predetermined time period.

6. The vapor release system defined in claim 1, wherein the system components are arranged in said container in a vertical orientation having a cannister form.

7. The vapor release system defined in claim 1, wherein the material components are arranged in said container in a horizontal elongated pouch-like orientation.

8. The vapor release system defined in claim 1, wherein said vaporizable material is a fragrant material selected from the group consisting of essential oils, synthetic aromatic material, solvents and combinations thereof.

9. The system defined in claim 8, wherein said vaporizable material is menthol essential oil dissolved in a solvent.

10. The system defined in claim 8, wherein said vaporizable material is ethyl acetate synthetic aromatic material dissolved in a suitable solvent.

11. The system defined in claim 1, wherein said vaporizable material is a disinfectant fluid.

12. The vapor release system defined in claim 1, wherein said container has rigid walls and said aperture is located in a cover at the container upper end.

13. The vapor release system defined in claim 1, wherein said container is in form of a pouch having flexible outer walls, and said aperture is located in one of the walls.

14. The vapor release system defined in claim 1, wherein said permeable barrier has a porosity of 1–110 cfm/ft$^2$ per 0.5 inch water differential pressure.

15. A vapor release system for dispensing a fragrance vapor from a vaporizable liquid in a controlled manner, comprising:
   (a) a hermetically sealable container;
   (b) a porous reservoir material provided within said container, said material having a void fraction volume of at least 75% and containing a vaporizable liquid fragrance material; said reservoir material having capillarity sufficient to continuously move the vaporizable material to an exposed surface of said reservoir material at a slow rate which prevents flooding or leaking of liquid from the reservoir material;
   (c) a plenum space provided within said container adjacent the exposed surface of said reservoir material;
   (d) a permeable barrier material located adjacent said plenum so tat said plenum space is located between the reservoir material and the permeable barrier, said permeable barrier having a porosity of 1–100 cfm/ft$^2$/0.5 in. water differential pressure;
   (e) an impermeable barrier material containing at least one aperture and located adjacent said permeable barrier, whereby said permeable barrier and said aperture in the impermeable barrier provide a combination permitting vapors to escape from the plenum at a predetermined low rate so that the vaporizable fragrance liquid is absorbed in capillaries in said porous reservoir material and is controllably evaporated from the reservoir into said plenum and then passed at a controlled rate through the permeable barrier and then through the aperture to the surrounding atmosphere.

16. A method for releasing vapors from a vaporizable liquid in a container to the surrounding atmosphere in a controlled manner, comprising the steps of:

(a) providing a vaporizable lqiuid material having a desired threshold of perceptibility in terms of air concentration in a selected volume of an absorbent reservoir material, the reservoir material having a total volume and void percentage sufficient to retain a desired volume of the liquid material;

(b) selecting a predetermined time period required for the vaporizable liquid to be evaporated and dispersed from the reservoir material;

(c) providing a permeable barrier material having a gas permeability of 1-100 cfm/sq.ft./0.5 in. water differential pressure near an exposed outer surface of the reservoir material so as to provide a plenum space therebetween;

(d) providing an impermeable barrier material having at least one aperture of controlled total area adjacent the permeable barrier material;

(e) enclosing the selected reservoir and permeable barrier materials in an appropriately sized hermetically sealable container, and providing a removable seal covering said aperture; and (f) removing the seal and allowing the vaporizable liquid contained in the reservoir material to evaporate and pass successively out through the plenum space, the permeable barrier and the aperture and be released at a desired controlled rate into the surrounding ambient air.

17. The vapor release method according to claim 16, including providing the exposed outer surface of the reservoir material adjacent the plenum to be at least about 50 times the aperture total area.

* * * * *